(12) United States Patent
Kojima et al.

(10) Patent No.: US 7,567,873 B2
(45) Date of Patent: Jul. 28, 2009

(54) NONDESTRUCTIVE INSPECTION METHOD AND APPARATUS FOR A SURFACE PROCESSED BY SHOT PEENING

(75) Inventors: Takashi Kojima, Ebina (JP); Masao Kumagai, Machida (JP); Kiyoshi Hoshikawa, Yokohama (JP); Shozo Ishibashi, Tokyo (JP)

(73) Assignee: Fuji Manufacturing Co., Ltd., Tokyo (JP)

( * ) Notice: Subject to any disclaimer, the term of this patent is extended or adjusted under 35 U.S.C. 154(b) by 162 days.

(21) Appl. No.: 11/727,238

(22) Filed: Mar. 26, 2007

(65) Prior Publication Data
US 2008/0001609 A1 Jan. 3, 2008

(30) Foreign Application Priority Data
Jun. 22, 2006 (JP) ............................. 2006-173061

(51) Int. Cl.
*G01B 5/30* (2006.01)
(52) U.S. Cl. ..................... 702/35; 73/779; 324/229; 324/232; 702/42; 702/83
(58) Field of Classification Search ............... 702/35, 702/42, 81–83, 183, 185; 324/232, 239, 324/632; 73/779
See application file for complete search history.

(56) References Cited

U.S. PATENT DOCUMENTS

| 5,963,030 | A | * | 10/1999 | Stark ......................... 324/229 |
| 6,377,039 | B1 | * | 4/2002 | Goldfine et al. ............. 324/232 |
| 7,188,532 | B2 | * | 3/2007 | Goldfine et al. ............... 73/779 |

OTHER PUBLICATIONS

Method and Effect of Shot Peening, Fatigue Strength of Metal and residual stress, by Shot Peening Technical Association, ed.1997, pp. 48-51.

* cited by examiner

*Primary Examiner*—John H Le
(74) *Attorney, Agent, or Firm*—Shlesinger, Arkwright & Garvey LLP

(57) ABSTRACT

An inspection method and an inspection apparatus that can easily measure a distribution of residual stress on a surface processed by shot peening, including a state of distribution in a depth direction of a material to be treated in a relatively short time without destroying the material to be treated. A coil provided in the inspection circuit is arranged on a surface processed by shot peening of the inspection target, an alternating current signal is input to the inspection circuit with changing a frequency so that frequency response characteristics of impedance of the inspection circuit is measured and acquired as inspection target data, and the inspection target data is compared to frequency response characteristics of impedance acquired from a sample of which a state of generation of residual stress is found.

12 Claims, 13 Drawing Sheets

NONDESTRUCTIVE INSPECTION METHOD AND APPARATUS FOR A SURFACE PROCESSED BY SHOT PEENING

BACKGROUND OF THE INVENTION

1. Field of the Invention

The present invention relates to a nondestructive inspection method and nondestructive inspection apparatus for inspecting the generation status of residual stress nondestructively in a steel material on which a treatment of shot peening was processed, more particularly relates to a nondestructive inspection method and nondestructive inspection apparatus appropriate for the inspection of surfaces processed by shot peening with fine particle shots with a diameter of tens of μm.

2. Description of the Prior Art

When a surface treatment of a steel material to be treated is performed by shot peening, plastic deformation of the surface of the material to be treated is implemented by a collision of shots and the result thereof; residual stress is generated.

This residual stress is a factor determining strength of the material to be treated, particularly bending strength, torsion strength, bending fatigue strength, torsion fatigue strength, and wear resistance. One purpose of shot peening is to modify a surface through generation of residual stress, therefore, an inspection of the state of generation of residual stress is one of important indices for quality control.

There are two known general methods for measuring the residual stress: a destructive method in which dimensional changes due to a release of the stress are accurately measured while removing an object to be treated which is processed by shot peening successively and a nondestructive method using X-ray analysis.

The destructive method among these methods measures residual stress by measuring deformation of the material to be treated due to reduction of a layer to be processed (residual stress generation layer) by removal of the surface of the material to be treated through electropolishing or chemical polishing, but the residual stress generated by shot peening, particularly by shot peening using fine particle shots appears only in a very shallow part near the surface of the material to be treated and may not be measured occasionally in the destructive method.

On the other hand, in the nondestructive inspection method using X-ray analysis, residual stress can be measured without destruction of the material to be treated, but an X-ray valid penetration depth is only several μm from the surface, so a state of residual stress can be inspected only at an uppermost surface of the material to be treated, but cannot be inspected in a depth direction.

To measure a distribution of residual stress in the such depth direction, it is necessary to calculate, under assumption based on material mechanics, the residual stress from deformation of the material to be treated that depends on changes in the cross section area (thickness) of the material to be treated by such as chemical polishing or cutting in the destructive method. However, as described above, in shot peening, particularly in shot peening using fine particles, residual stress generates in a relatively shallow part from the surface, so it may not be measured by the destructive method. The assumption based on material mechanics used in the above method cannot reproduce the state of stress in the material to be treated which should be measured with high fidelity, and the precision is reduced in that measurements are made while changing the thickness of the material to be treated as well as residual stress.

To improve the reliability of the measurement results, "a window method", which measures a state of residual stress in the depth direction of the material to be treated by X-ray analysis, is suggested.

The window method measures residual stress in the depth direction by X-ray analysis while removing a minute circular or square area called a window instead of the entire surface of an inspection target through chemical polishing or electropolishing; this method can measure the distribution of residual stress in the material to be treated without changing the distribution.

According to the window method, a distribution of residual stress can be measured in the depth direction of the material to be treated without being restricted by the X-ray valid penetration depth and measurement results are accurate, further, the reliability is improved.

However, this inspection of a state of residual stress by X-rays requires destruction of the material to be treated (even if it is a very small or minute opening), so the whole products cannot be inspected and the inspection must be carried out as sampling inspection.

To measure the distribution of the residual stress in the depth direction of the material to be treated according to the window method, it is necessary to repeat the procedure in which the window part is polished until it is reached to a specified depth and then an X-ray inspection is carried out, thereby a lot of works and times are required therefor.

In consideration of the problems of conventional methods of inspecting residual stress, as an inspection method for the material to be treated having a surface processed by shot peening, it is desired to develop an inspection method and inspection apparatus that can easily inspect the state of generation of residual stress in the depth direction in a relatively short time without destruction of the material to be treated; and if such an inspection method and inspection apparatus of this type are realized, the whole products can be inspected.

However, there is currently no inspection method and inspection apparatus of this type, thus a sampling inspection must be performed and if a prescribed faulty rate is generated in the sampling inspection, the whole products manufactured on the line is discarded for quality control, for example. In this method, however, yields are reduced because correctly processed products are also discarded, and incorrectly processed products may be included even if the faulty rate falls within an allowable range.

SUMMARY OF THE INVENTION

The present invention is addressed to solve the problems of the above prior art, and provide an inspection method and inspection apparatus that can easily measure a distribution of residual stress of a surface processed by shot peening including a distribution state of residual stress in the depth direction in a relatively short time without destroying the material to be treated.

To achieve the above object, a nondestructive inspection method for a surface processed by shot peening according to the present invention in which a steel material processed by shot peening is used as an inspection target to inspect residual stress, is characterized in that:

a coil provided in an inspection circuit is arranged on a surface processed by shot peening of a sample of which a state of generation of residual stress is found, the sample being made of the same material as the inspection target, an alternating current signal is input to the inspection circuit with changing a frequency, and frequency response characteristics of impedance of the inspection circuit is measured and acquired as sample data;

the coil provided in the inspection circuit is arranged on a surface of the inspection target, an alternating current signal is input to the inspection circuit with changing a frequency, and frequency response characteristics of impedance of the inspection circuit is measured and acquired as inspection target data; and the inspection target data is compared to the sample data and, based on the state of generation of residual stress found in the sample, a state of generation of residual stress in the inspection target is inspected.

In the inspection method, changes in a phase angle θ between a voltage and a current generated in the inspection circuit depending on changes in the frequency of the input signal are measured as the frequency response characteristics of the impedance.

The coil provided in the inspection circuit is arranged on a surface of a reference material not processed by shot peening, the reference material being made of the same material as the inspection target, and an alternating signal is input to the inspection circuit with changing a frequency to acquire changes in a phase angle $θ_{non-shot}$ between a voltage and a current in the inspection circuit as reference data; and a difference (Δθ) between the reference data and the sample data and a difference (Δθ) between the reference data and the inspection target data may be used to compare the sample data to the inspection target data.

A value indicating a peak of the difference of the phase angle (Δθ) with respect to changes in the frequency may be obtained as an extreme value ($Δθ_p$) so as to use the extreme value ($Δθ_p$) and/or a frequency ($f_p$) giving the extreme value ($Δθ_p$) as comparison points for the inspection target data and the sample data.

A depth b of a residual stress generation layer formed on the inspection target by shot peening may be inspected or measured based on comparison between the inspection target data and the sample data. Furthermore, a magnetic permeability $μ_1$ and/or a resistivity $ρ_1$ of the residual stress generation layer may be inspected or measured based on comparison between the inspection target data and the sample data.

A nondestructive inspection apparatus for a surface processed by shot peening in which steel material processed by shot peening is used as an inspection target to inspect residual stress is characterized by comprising:

an inspection circuit including a coil arranged on the inspection target;

an inspection signal generation means for outputting an alternating current signal to the inspection circuit while changing a frequency;

a measurement means for measuring frequency response characteristics of impedance of the inspection circuit;

a recording means for recording frequency response characteristics of impedance measured by arranging the coil of the inspection circuit on a sample of which a state of generation of residual stress is found, as sample data, the sample being made of the same material as the inspection target;

a comparison means for comparing inspection target data with the sample data recorded in the recording means, the inspection target data being the frequency response characteristics of impedance of the inspection circuit measured by arranging the coil of the inspection circuit on the inspection target; and a determination means for determining a state of generation of residual stress in the inspection target based on a state of generation of residual stress found in the sample by using comparison results by the comparing means.

In the inspection apparatus having the above constitutions, the measurement means may measure, as the inspection target data, changes in a phase angle θ between a voltage and a current generated in the inspection circuit depending on changes in a frequency f of the input signal; and the recording means may record, as the sample data, changes in a phase angle θ between voltage and current generated in the inspection circuit in the sample depending on changes in the frequency f of the input signal.

The recording means may record, as reference data, changes in a phase angle $θ_{non-shot}$ between a voltage and a current generated in the inspection circuit in a reference material not processed by shot peening, the reference material being made of the same material as the inspection target; and the comparing means may compare a difference between the reference data and the sample data to a difference between the reference data and the inspection target data.

A value indicating a peak of the difference of the phase angle Δθ with respect to changes in the frequency f may be obtained as an extreme value $Δθ_p$ so as to use the extreme value $Δθ_p$ and/or a frequency $f_p$ giving the extreme value $Δθ_p$ as comparison points for the inspection target data and the sample data.

The recording means may record, as the sample data, a relation of correspondence between changes in a depth b of the residual stress generation layer and frequency response characteristics of impedance of the inspection circuit changed depending on the changes in the depth of the residual stress generation layer; and the determination means may determine, according to comparison results by the comparing means, the depth b of the residual stress generation layer formed on a surface of an inspection target based on the relation of correspondence.

The recording means may record, as the sample data, a relation of correspondence between changes in a magnetic permeability $μ_1$ and/or a resistivity $ρ_1$ of the residual stress generation layer and frequency response characteristics of impedance of the inspection circuit changed depending on the changes in the magnetic permeability $μ_1$ and/or the resistivity $ρ_1$; and the determination means may determine, according to comparison results by the comparing means, determine the magnetic permeability $μ_1$ and/or the resistivity $ρ_1$ of the a residual stress generation layer formed on the surface of the inspection target based on the relation of correspondence.

The inventive inspection method and inspection apparatus having the inventive structure of the present invention described above can easily measure a state of residual stress of a surface processed by shot peening including a state of residual stress in the depth direction of the material to be treated in a relatively short time without destroying the material to be treated.

BRIEF DESCRIPTION OF THE DRAWINGS

The objects and advantages of the invention will become apparent from the following detailed description of preferred embodiments thereof provided in connection with the accompanying drawings in which.

DETAILED DESCRIPTION OF THE PREFERRED EMBODIMENT

Next, embodiments of the present invention will be described below.

Prerequisite Principles

Overview of the Present Invention

For a surface to be inspected, which is processed by shot peening in a nondestructive inspection method according to the present invention, particularly for a surface processed by shot peening with fine particles having a diameter of tens of µm as shots, residual stress generates at a relatively shallow depth, that is tens of µm from the surface of the material to be treated. Accordingly, in the inspection of a distribution state of residual stress on the surface processed by shot peening, if a generation state of residual stress in a range of several µm to 100 µm in depth from the surface can be measured, an objective of the inspection can be achieved.

An inventor of the present invention experimentally found that, when a ferromagnetic steel material is used as an inspection target, if an alternating current signal is input to a coil (an inspection circuit including the coil) arranged so that a magnetic field generating direction is orthogonal to a residual stress generation surface of the inspection target while changing a frequency, the frequency response characteristics of impedance of the coil (inspection circuit) characteristically changes depending on the difference of a generation state of residual stress at depths of about several µm to 100 µm from the surface of the inspection target.

It was recognized that, in particular, the frequency response characteristics of a change $\Delta\theta$ in a phase angle $\theta$ (difference between a phase angle $\theta_{shot}$ measured after shot peening and a phase angle $\theta_{non-shot}$ measured before shot peening) between a voltage and a current in the inspection circuit is significantly changed.

The present invention originates from the fact that, focusing on a relation of correspondence between the steel material processed by shot peening and the frequency response characteristics of impedance of the inspection circuit including the coil, the relation of correspondence can be used to inspect the state of generation of residual stress in the material to be treated, which is steel material surface-treated-by shot peening.

Relation of correspondence between the residual stress and the frequency response characteristics of impedance The following shows a relation between the state of generation of residual stress in the steel material and the frequency response characteristics of impedance of the inspection circuit including the coil.

Derivation of a Relation of Correspondence by Calculation

Conditions of Calculation

Figure 1:
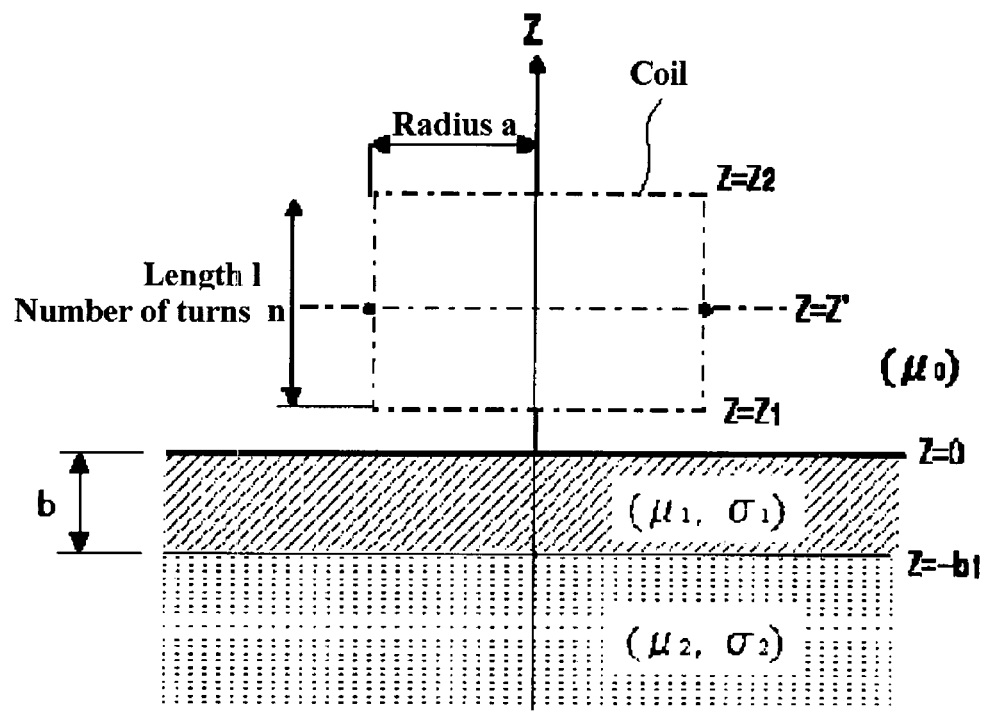
FIG. 1 is an explanatory drawing of a model for analyzing an inductance of a coil.

FIG. 1 shows a model for analyzing the inductance of the coil arranged on the material to be treated.

As shown in FIG. 1, assuming that an electric characteristic of the material to be treated not processed by shot peening is uniform, magnetic permeability and conductivity of the material to be treated are defined as $\mu_2$ and $\sigma_2$, respectively.

When the material to be treated is processed by shot peening, a layer in which residual stress is generated (residual stress generation layer) in a range from the surface to a depth b is assumed to be generated and, for simplicity, electric characteristics of the material to be treated are assumed to be uniformly changed to magnetic permeability $\mu_1$ and conductivity $\sigma_1$, respectively, in the residual stress generation layer.

A radius, a length, and number of turns of a coil to be inspected are defined as a, 1, and n, respectively.

A z-axis is provided so as to be orthogonal to a sample and aligned with the center axis of the coil and its origin is positioned on the surface of the material to be treated, then the coordinate of the lower end of the coil is defined as $z_1$ and that of the upper end of the coil is defined as $z_2$.

Method for Calculating Impedance Z and the Phase Angle $\theta$

In the analysis model in FIG. 1, an expression for calculating impedance Z and the phase angle $\theta$ is derived as shown below.

First, the Maxwell equation underlying the following calculation is shown below.

[Expression 1]

$$\nabla \times H = J + \frac{\partial D}{\partial t} \quad (1)$$

[Expression 2]

$$\nabla \times E = -\frac{\partial B}{\partial t} \quad (2)$$

When the frequency of a sinusoidal alternating current flowing through the coil is tens of MHz or less, a displacement current is negligible and Expression (1) is represented as follows.

[Expression 3]

$$\nabla \times H = J \quad (3)$$

This is a governing equation for the outside of the conductive sample. The following expression is derived from Expression (2), Expression (3), and the Ohm's law.

[Expression 4]

$$\nabla \times \nabla \times H = -\mu\sigma j\omega H \quad (4)$$

Where, $\omega$ is an angular frequency of the sinusoidal alternating current and j is an imaginary unit. This expression is the governing expression for the inside of the conductive sample.

Here, cylindrical coordinates $(r,\phi,z)$ is introduced to define vector potential A satisfying $\mathbf{H}=\nabla\times\mathbf{A}$. A only has $\phi$ direction component $A_{100}$, because its system is rotationally symmetric. Accordingly, if $A_{100}$ is expressed as A with its subscript omitted, the governing equation for the outside of the conductive sample is represented as follows according to Expression (3).

[Expression 5]

$$\frac{\partial}{\partial r}\frac{1}{r}\frac{\partial}{\partial r}(rA) + \frac{\partial^2 A}{\partial z^2} = -J \quad (5)$$

The governing equation for the inside of the conductive sample is represented as follows according to Expression (4).

[Expression 6]

$$\left(r\frac{\partial}{\partial r}\frac{1}{r}\frac{\partial}{\partial r} + \frac{\partial^2}{\partial z^2} - j\omega\mu\sigma\right)(rA) = 0 \quad (6)$$

Figure 2:
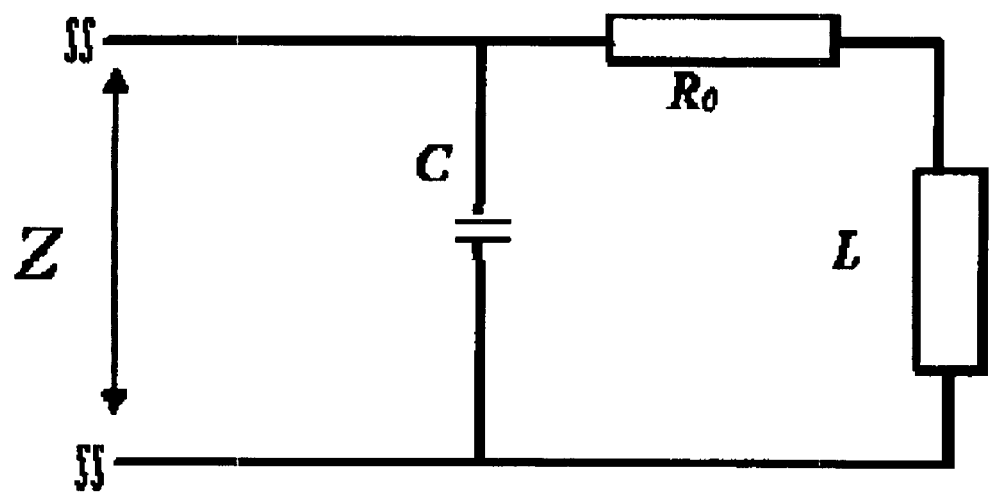
FIG. 2 is a drawing of an equivalent circuit of an inspection circuit.

If Expressions (5) and (6) described above are solved with the boundary conditions in FIG. 2 satisfied in order to obtain A, the inductance of the coil is thereby obtained. An analysis of this type has been solved by Onoue (Morio Onoue: "Analysis of a Finite-Length Solenoid Coil Close to a Conductor," The Journal of the Institute of Electrical Engineers of Japan, vol. 88, pp. 1894 to 1902 (1968)). Inductance L of the coil is represented as the following expression according to this solution.

[Expression 7]

$$L = \frac{2\pi n\mu_0 a}{lI}\int_{z_1}^{z_2}(A)_{r=a}\,dz = L_0(\nu-\lambda) \quad (7)$$

Where,

[Expression 8]

$$L_0 = \frac{\mu_0\pi a^2 n^2}{l} \quad (8)$$

$$\nu = 2\int_0^\infty J_1^2(\zeta a)\left(\frac{1}{\zeta} - \frac{1}{\zeta^2 l} + \frac{1}{\zeta^2 l}e^{-\zeta l}\right)d\zeta$$

$$\lambda = \frac{1}{l}\int_0^\infty \frac{1}{\zeta^2}J_1^2(\zeta a)(e^{-\zeta z_2}-e^{-\zeta z_1})^2$$

$$\left\{\frac{\left(-\frac{\mu_1}{\mu_0}+\frac{\eta_1(\zeta)}{\zeta}\right)\left(\frac{\mu_2}{\mu_1}+\frac{\eta_2(\zeta)}{\eta_1\zeta}\right)+}{\left(\frac{\mu_1}{\mu_0}+\frac{\eta_1(\zeta)}{\zeta}\right)\left(-\frac{\mu_2}{\mu_1}+\frac{\eta_2(\zeta)}{\eta_1\zeta}\right)e^{2\eta_1(\zeta)b_1}}\right\} d\zeta$$

$$\eta_1(\zeta) = \sqrt{\zeta^2 + j\omega\mu_1\sigma_1}, \quad \eta_2(\zeta) = \sqrt{\zeta^2 + j\omega\mu_2\sigma_2}$$

Impedance Z measured when a current flow through the coil arranged on the sample surface includes effects of resister component $R_0$ of elemental coil wires and capacity component C of the cable connecting between the coil and the inspection apparatus in addition to inductance L of the coil. If the equivalent circuit in FIG. 2 is used as a model, impedance Z is calculated by the following expression.

[Expression 9]

$$Z = \frac{\frac{R_0+\text{Re}(j\omega L)}{\omega C} - j\{(R_0+\text{Re}(j\omega L))^2 + \text{Im}(j\omega L)\left(\text{Im}(j\omega L)-\frac{1}{\omega C}\right)\}}{\omega C\left\{(R_0+\text{Re}(j\omega L))^2 + \left(\text{Im}(j\omega L)-\frac{1}{\omega C}\right)^2\right\}} \quad (9)$$

If the absolute value and phase of the impedance are expressed as |Z| and $\theta$, respectively, |Z| and $\theta$ are calculated by the following expressions.

[Expression 10]

$$|Z| = \frac{\sqrt{\left(\frac{R_0 + \text{Re}(j\omega L)}{\omega C}\right) + \{(R_0 + \text{Re}(j\omega L))^2 + \text{Im}(j\omega L)\left(\text{Im}(j\omega L) - \frac{1}{\omega C}\right)\}^2}}{\omega C\left\{(R_0 + \text{Re}(j\omega L))^2 + \left(\text{Im}(j\omega L) - \frac{1}{\omega C}\right)^2\right\}} \quad (10)$$

[Expression 11]

$$\theta = \tan^{-1}\left(\frac{-\omega C\{(R_0 + \text{Re}(j\omega L))^2 + \text{Im}(j\omega L)\left(\text{Im}(j\omega L) - \frac{1}{\omega C}\right)\}}{R_0 + \text{Re}(j\omega L)}\right) \quad (11)$$

If Expressions (10) and (11) obtained as described above are used, the relation between the feature of the electromagnetic characteristic of the surface of the material to be treated and the frequency response characteristics of impedance measured by the inspection circuit including the coil arranged on the surface of the material to be treated can be determined.

A Relation of Correspondence Obtained from the Expressions Described Above

According to the analysis model and expressions described above, a presence of the following relation of correspondence between a residual stress generation layer formed on the surface of the material to be treated and the frequency response characteristics of the impedance can be recognized.

Prerequisites for Calculation

In derivation of the relation of correspondence through calculation, changes $\Delta|Z|$ in the absolute impedance value and changes $\Delta\theta$ in the phase angle before and after shot peening is defined as shown below.

$$\Delta|Z| = |Z|_{shot} - |Z|_{non\text{-}shot} \quad (12)$$

$$\Delta\theta = \theta_{shot} - \theta_{non\text{-}shot} \quad (13)$$

Where, $|Z|_{non\text{-}shot}$ and $\theta_{non\text{-}shot}$ denote the absolute impedance value and phase angle measured in the inspection circuit before the material to be treated is processed by shot peening.

Before the shot peening process, there is no residual stress generation layer deformed plastically on the material to be treated, and magnetic permeability $\mu_1$ near the surface of the material to be treated is equal to magnetic permeability $\mu_2$ inside the material to be treated ($\mu_1 = \mu_2$), moreover, conductivity $\sigma_1$ near the surface of the material to be treated is equal to conductivity $\sigma_2$ inside the material to be treated ($\sigma_1 = \sigma_2$).

$|Z|_{shot}$ and $\theta_{shot}$ denote the absolute impedance value and the phase angle measured in the inspection circuit after when the material to be treated is processed by shot peening.

Calculation is performed, assuming that shot peening generates a plastic deformation on the surface of the material to be treated, so magnetic permeability $\mu_1$ near the surface of the material to be treated becomes different from magnetic permeability $\mu_2$ inside the material to be treated ($\mu_1 \neq \mu_2$), moreover, conductivity $\sigma_1$ near the surface of the material to be treated becomes different from conductivity $\sigma_2$ inside the material to be treated ($\sigma_1 \neq \sigma_2$), and such a residual stress generation layer is formed at depth b (b≠0) from the surface of the material to be treated.

Calculated Relation of Correspondence

General Relation of Correspondence (a) Frequency response characteristics of $\Delta|Z|$ and $\Delta\theta$ in general steel materials In many steel materials, it is found that a plastic deformation significantly reduces magnetic permeability and slightly reduces conductivity.

Figure 6:
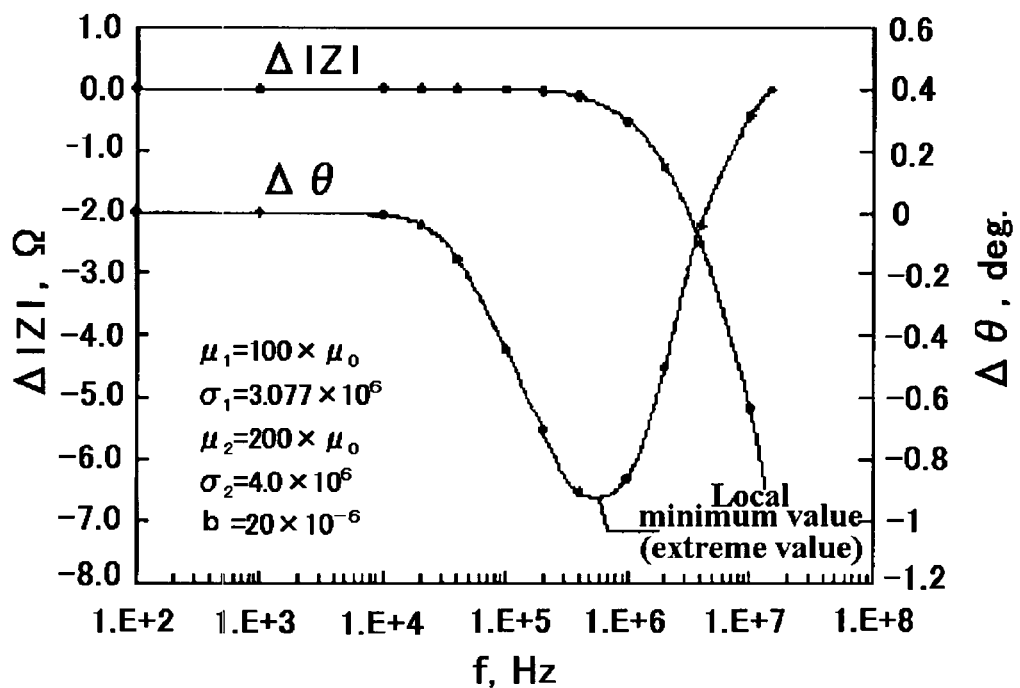
FIG. 6 is a graph showing results of calculation of the frequency response characteristics of $\Delta|Z|$ and $\Delta\theta$ when a general steel material processed by shot peening is a measurement target.

FIG. 6 shows the relation between frequency f and $\Delta|Z|$ and the relation between frequency f and $\Delta\theta$ as a result of calculation based on this fact, assuming that a residual stress generation layer with a depth of 20 μm is formed after shot peening, the magnetic permeability is decreased from 200×$\mu_0$ to 100×$\mu_0$, and the conductivity is decreased from $4.0\times10^6$ (1/Ωm) to $3.08\times10^6$ (1/Ωm) in the residual stress generation layer.

As shown in FIG. 6, $\Delta|Z|$ is suddenly decreased in a high-frequency area. On the other hand, $\Delta\theta$ is decreased and then increased, that is, $\Delta\theta$ has a local minimum value (extreme value) which is a peak of the reduction of $\Delta\theta$.

(b) Frequency Response Characteristics of $\Delta|Z|$ and $\Delta\theta$ in Austenitic Steel Materials In stainless steel or a steel material containing retained austenite after quenching, a plastic deformation makes austenite transformed into martensite, thereby the magnetic permeability is increased.

Figure 7:
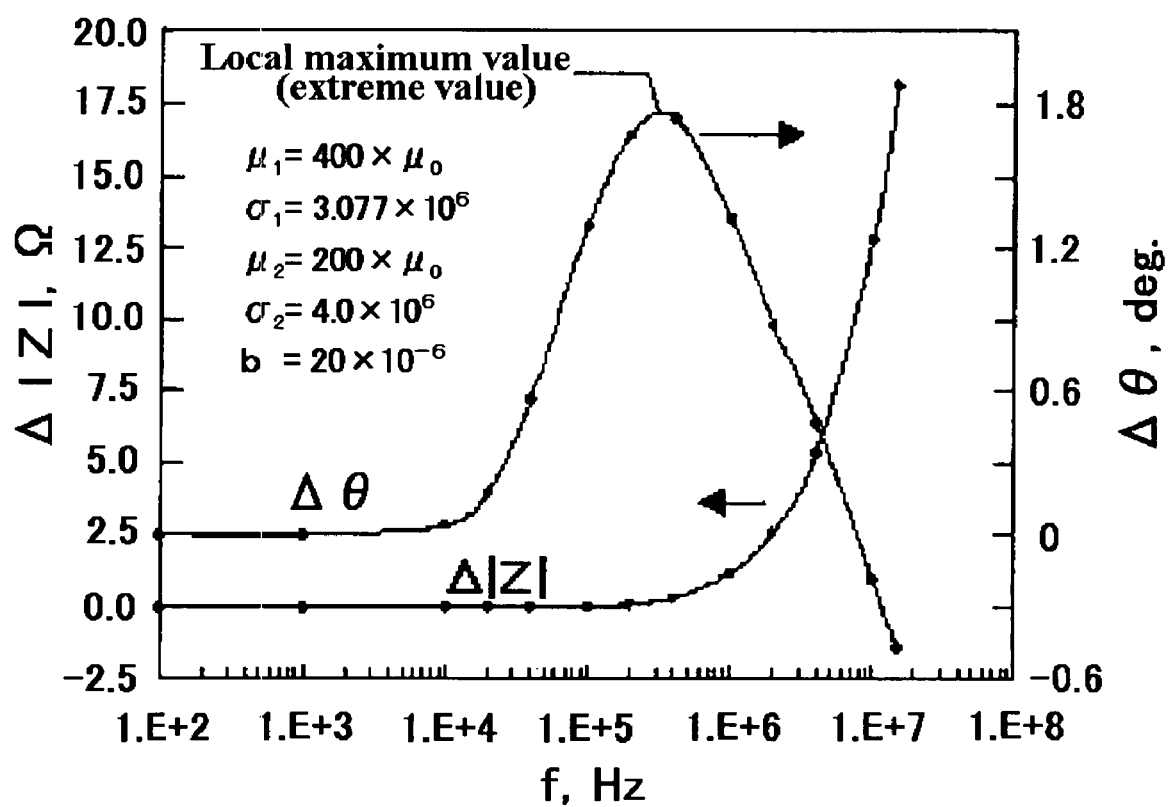
FIG. 7 is a graph showing results of calculation of the frequency response characteristics of $\Delta|Z|$ and $\Delta\theta$ when a austenite steel material processed by shot peening is a measurement target.

FIG. 7 shows the relation between frequency f and $\Delta|Z|$ and the relation between frequency f and $\Delta\theta$ as a result of calculation based on this fact, assuming that the magnetic permeability is increased from 200×$\mu_0$ to 400×$\mu_0$ and the conductivity is decreased from $4.0\times10^6$ (1/Ωm) to $3.08\times10^6$ (1/Ωm) in the residual stress generation layer at a depth of 20 μm after shot peening.

As shown in FIG. 7, unlike the results of general steel materials described above, $\Delta|Z|$ is suddenly increased in a high-frequency area and $\Delta\theta$ is increased and then decreased, that is, $\Delta\theta$ has a local maximum value (extreme value) which is a peak of the increase.

The relation between f and $\Delta\theta$ (hereinafter, referred to as the f-$\Delta\theta$ diagram) significantly changes depending on characteristic feature of the electromagnetic characteristic of the sample surface.

Figure 8:
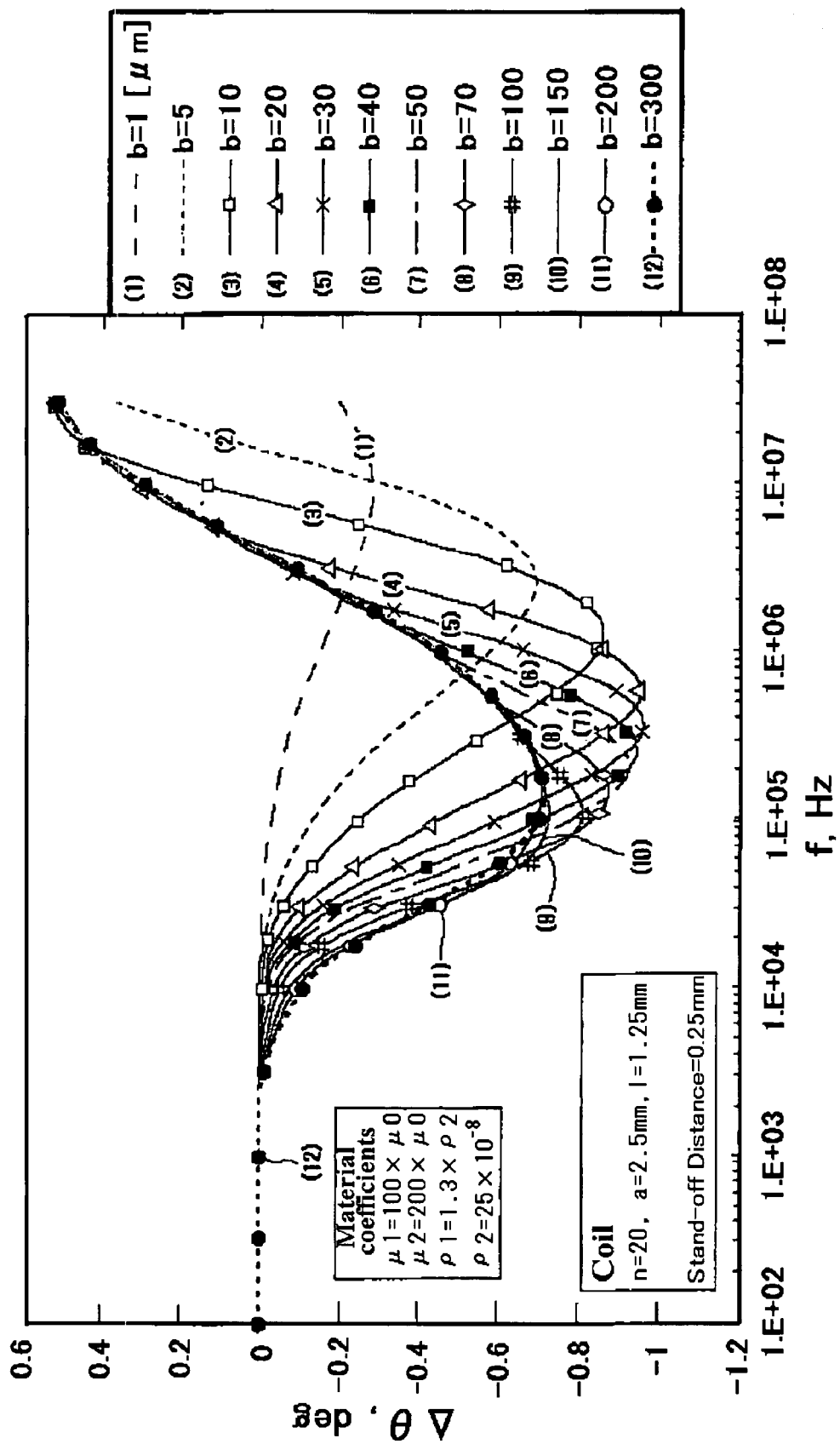
FIG. 8 is a graph showing results of calculation of f-$\Delta\theta$ curves when the depth of a residual stress generation layer is changed ($\mu_1=100\times\mu_0$: $\mu_2=200\times\mu_0$)

Depth at which Residual Stress is Generated and Frequency Response Characteristics of $\Delta\theta$ FIG. 8 is an f-$\Delta\theta$ diagram calculated when the depth b of the residual stress generation layer is changed on the assumption that the magnetic permeability is decreased from 200×$\mu_0$ to 100×$\mu_0$ and the conductivity is decreased from $4.0\times10^6$ (1/Ωm) to $3.08\times10^6$ (1/Ωm) in the residual stress generation layer.

When the depth of the residual stress generation layer is increased in the range of 1 μM to 100 μm of the depth of the residual stress generation layer, frequency $f_P$ at which the local minimum value is given in the f-$\Delta\theta$ diagram shifts to a lower-frequency side accordingly.

When the depth of the residual stress generation layer is increased in the range of 1 μm to 20 μm of the depth of the residual stress generation layer, the absolute local minimum value $|\Delta\theta_P|$ is also increased.

Similar calculation was performed in the following two cases.

Figure 9:
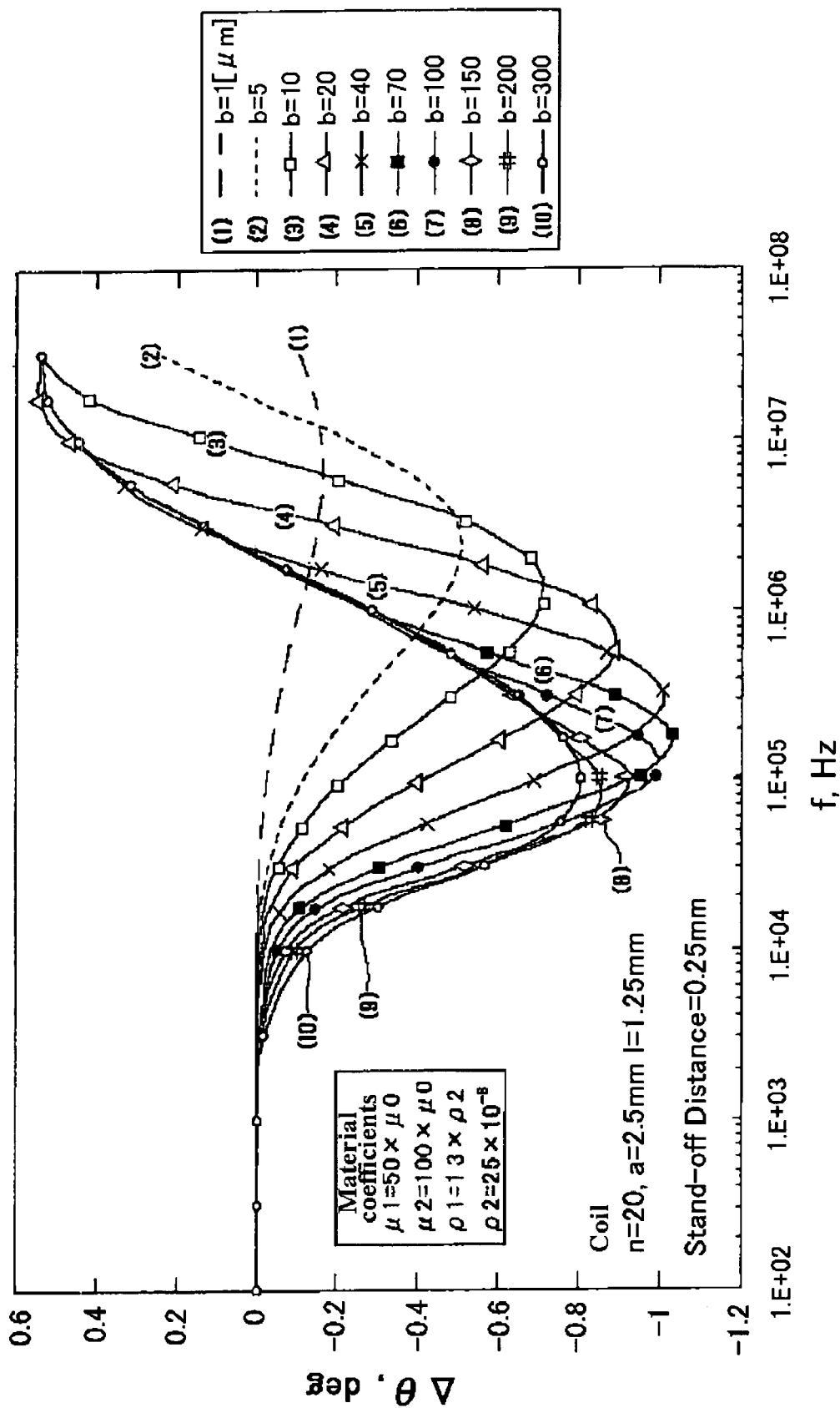
FIG. 9 is a graph showing results of calculation of f-$\Delta\theta$ curves when the depth of a residual stress generation layer is changed ($\mu_1=50\times\mu_0$; $\mu_2=100\times\mu_0$)
Figure 10:
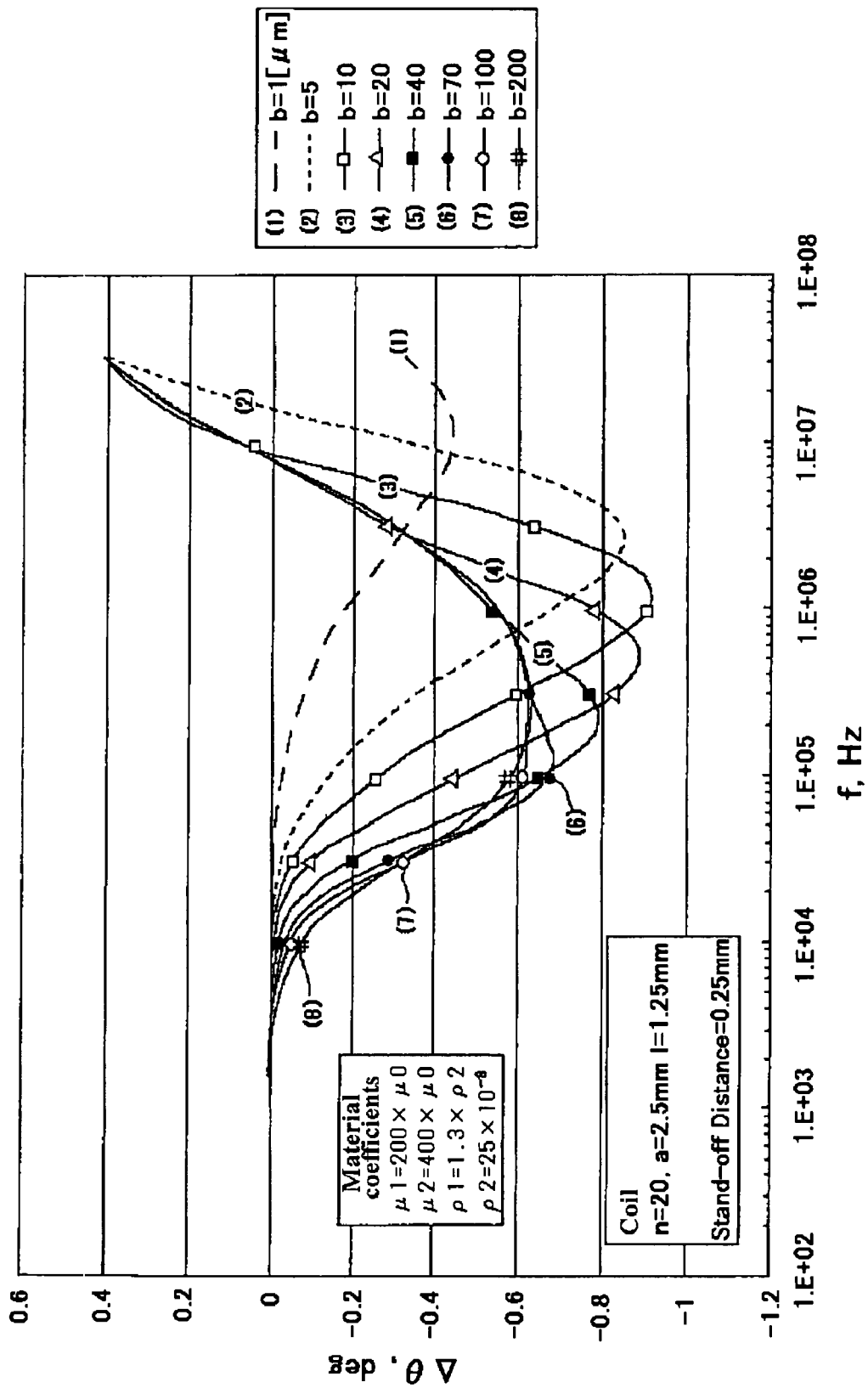
FIG. 10 is a graph showing results of calculation of f-$\Delta\theta$ curves when the depth of a residual stress generation layer is changed ($\mu_1=200\times\mu_0$; $\mu_2=400\times\mu_0$)

(1) When the magnetic permeability is decreased from 100×$\mu_0$ to 50×$\mu_0$ (2) When the magnetic permeability is decreased from 400×$\mu_0$ to 200×$\mu_0$ These results of calculation are shown in FIGS. 9 and 10, respectively.

As shown in the FIGS. 9 and 10, frequency $f_P$ showing the local minimum value apparently shifts to a lower-frequency side in the range of 1 µm to 150 µm of the depth of the residual stress generation layer in FIG. 9 (when the magnetic permeability is decreased from $100 \times \mu_0$ to $50 \times \mu_0$) or in the range of 1 µm to 70 µm in FIG. 10 (when the magnetic permeability is decreased from $400 \times \mu_0$ to $200 \times \mu_0$).

The absolute local minimum value $|\Delta\theta P|$ is increased corresponding to the increase of the depth of the residual stress generation layer in the range of 1 µm to 40 µm of the depth of the residual stress generation layer in FIG. 9 (when the magnetic permeability is decreased from $100 \times \mu_0$ to $50 \times \mu_0$) or in the range of 1 µm to 10 µm of the depth of the residual stress generation layer in FIG. 10 (when the magnetic permeability is decreased from $400 \times \mu_0$ to $200 \times \mu_0$).

Figure 11:
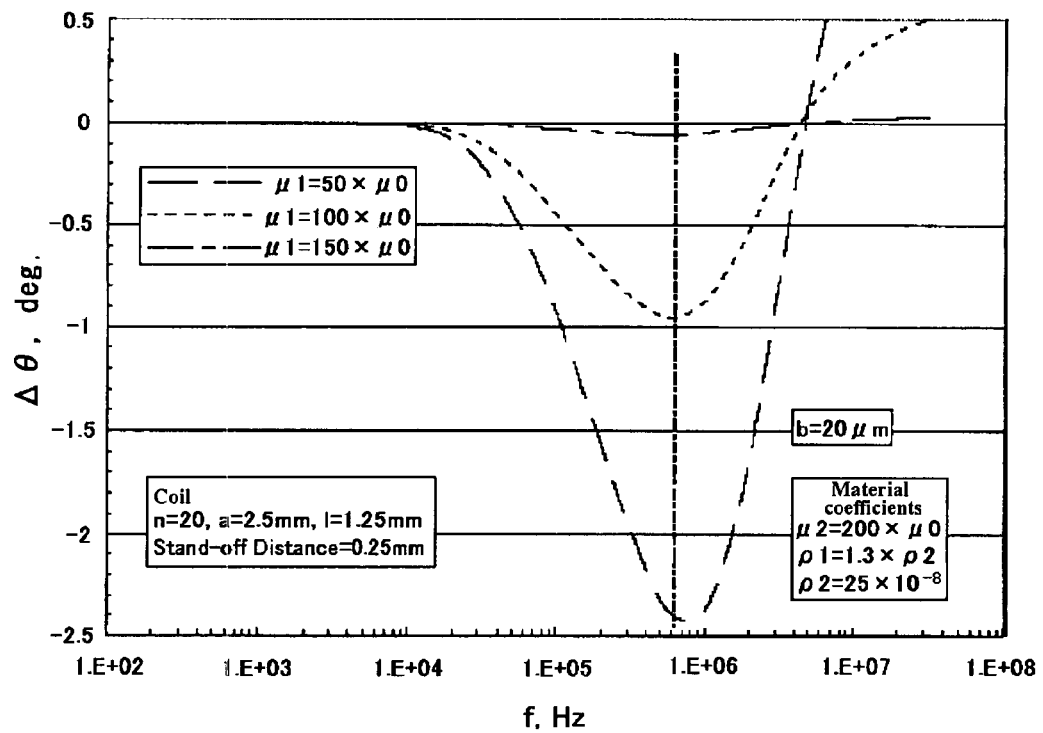
FIG. 11 is a graph showing results of calculation of f-$\Delta\theta$ curves when magnetic permeability is changed.

Changes in the Magnetic Permeability and Frequency Response Characteristics of $\Delta\theta$ FIG. 11 shows results of calculation of an effect of changes in the magnetic permeability on the f-$\Delta\theta$ diagram.

In FIG. 11, the following three cases with the depth of the residual stress generation layer of 20 µm and the conductivity decreasing from $4.0 \times 10^6$ (1/Ωm) to $3.08 \times 10^6$ (1/Ωm) are compared.
(1) When the conductivity is decreased from $200 \times \mu_0$ to $50 \times \mu_0$
(2) When the conductivity is decreased from $200 \times \mu_0$ to $100 \times \mu_0$
(3) When the conductivity is decreased from $200 \times \mu_0$ to $150 \times \mu_0$ When the magnetic permeability significantly is decreased, a local minimum value $\Delta\theta_P$ of $\Delta\theta$ is remarkably decreased. The local minimum value $\Delta\theta_P$ of $\Delta\theta$ is changed greatly depending on changes in the magnetic permeability, but frequency $f_p$ giving the local minimum value $\Delta\theta_P$ is changed slightly depending on the changes in the magnetic permeability.

Figure 12:
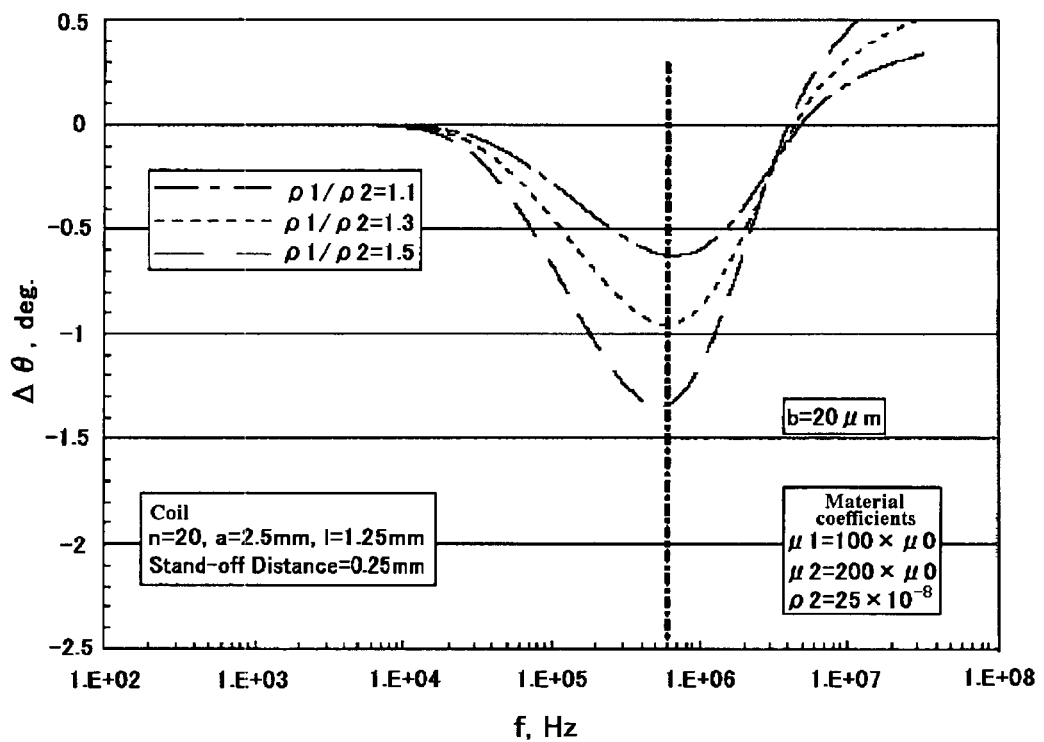
FIG. 12 is a graph showing results of calculation of f-$\Delta\theta$ curves when resistivity is changed.

Changes in the Resistivity and Frequency Response Characteristics of $\Delta\theta$ FIG. 12 shows results of calculation the effect of changes in the resistivity (reciprocal of the conductivity) on the f-$\Delta\theta$ diagram.

In FIG. 12, the following three cases when the depth of the residual stress generation layer is 20 µm and the magnetic permeability is decreased from $200 \times \mu_0$ to $50 \times \mu_0$ (1/Ωm) are compared.
(1) When the magnetic permeability is increased from $\rho_2$ (=$25 \times 10^{-8}$ ΩM) to $1.1 \times \rho_2$
(2) When the magnetic permeability is increased from $\rho_2$ (=$25 \times 10^{-8}$ Ωm) to $1.3 \times \rho_2$
(3) When the magnetic permeability is increased from $\rho_2$ (=$25 \times 10^{-8}$ Ωm) to $1.5 \times \rho_2$ When the resistivity is significantly increased, the local minimum value $\Delta\theta_P$ of $\Delta\theta$ is increased. The local minimum value of $\Delta\theta$ is changed greatly depending on changes in the magnetic permeability, but the frequency giving the local minimum value is changed slightly depending on the changes in the magnetic permeability.

Confirmation of the Relation of Correspondence by Actual Measurements

The presence of the relation of correspondence obtained by calculation is also proven by the experimental results shown below.

Actual Measurement Using SDK61 Steel as a Sample

As Embodiment 1, the following shows results of inspecting the state of generation of residual stress and the relation of correspondence between $\Delta\theta$ and $f_P$ as to SKD61 steel processed by shot peening with fine particles.

SKD61 steel (hardness: HRC48) is processed by shot peening with fine particles at four different shot injection speeds to create four samples with different states of generation of residual stress.

Figure 13:
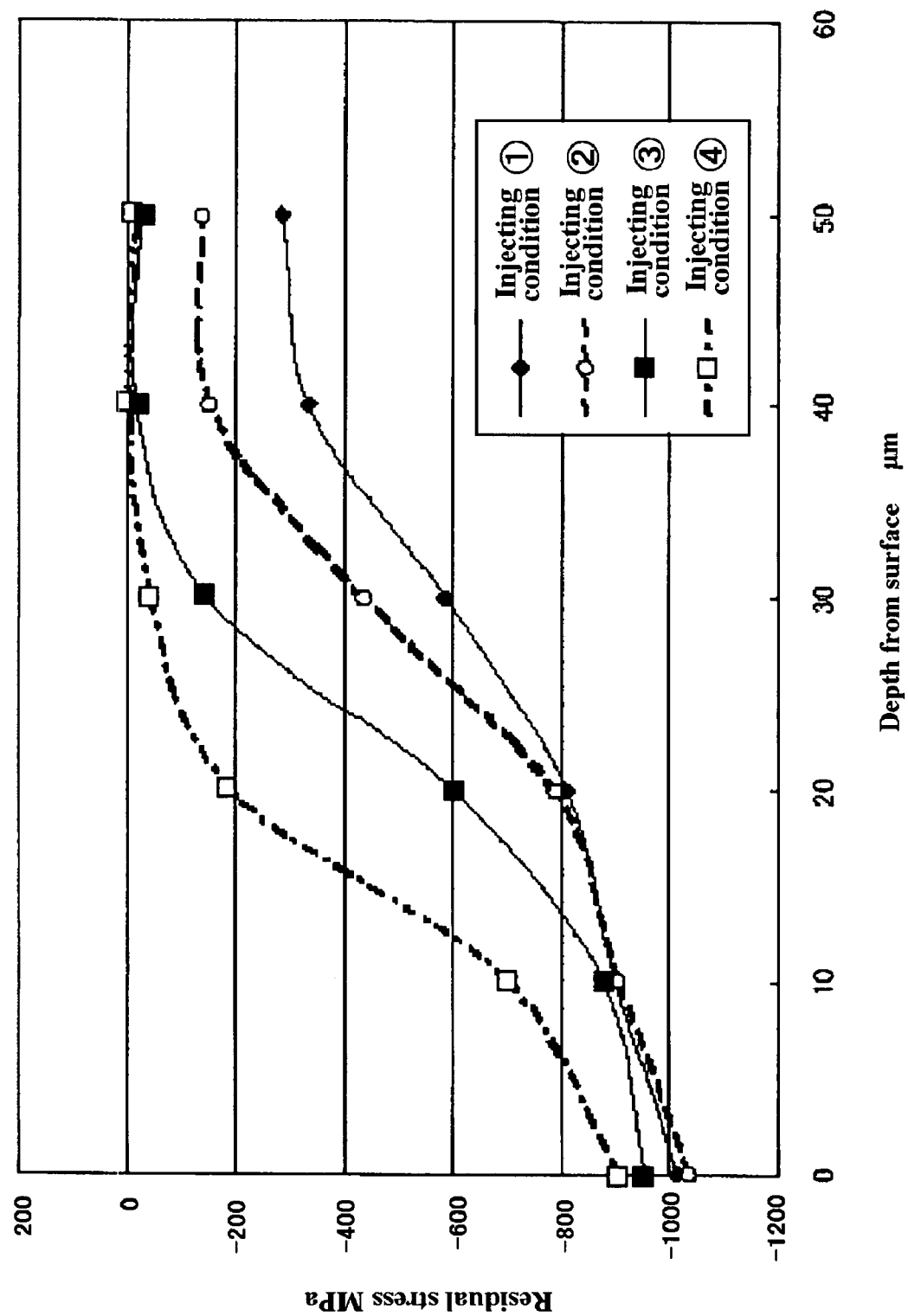
FIG. 13 is a graph showing the relation between the residual stress and the depth (measured by X-rays) for SDK61 steel materials processed by shot peening in different conditions.
Figure 14:
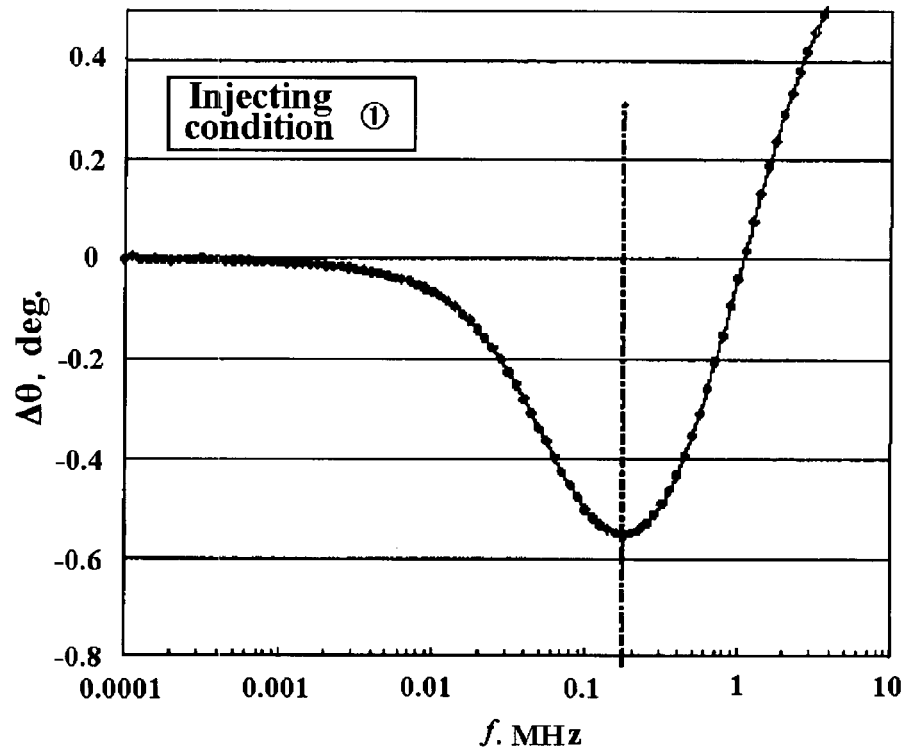
FIG. 14 is an f-$\Delta\theta$ diagram of SKD61 steel processed by shot peening in Injecting condition 1.
Figure 15:
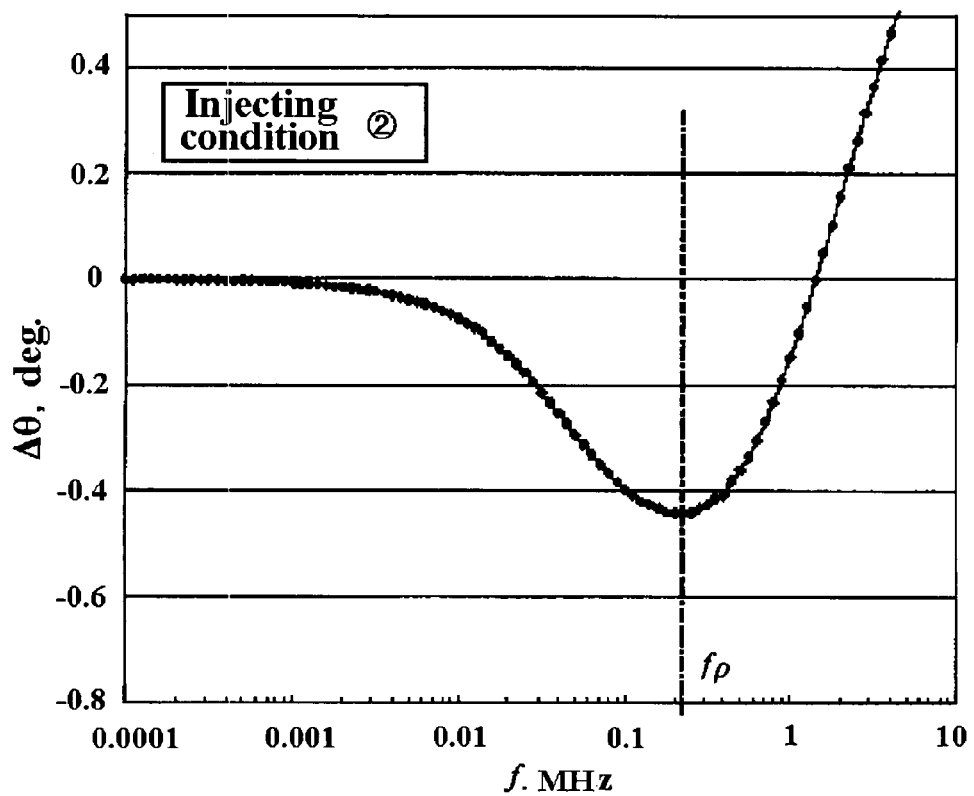
FIG. 15 is an f-$\Delta\theta$ diagram of SKD61 steel processed by shot peening in Injecting condition 2.
Figure 16:
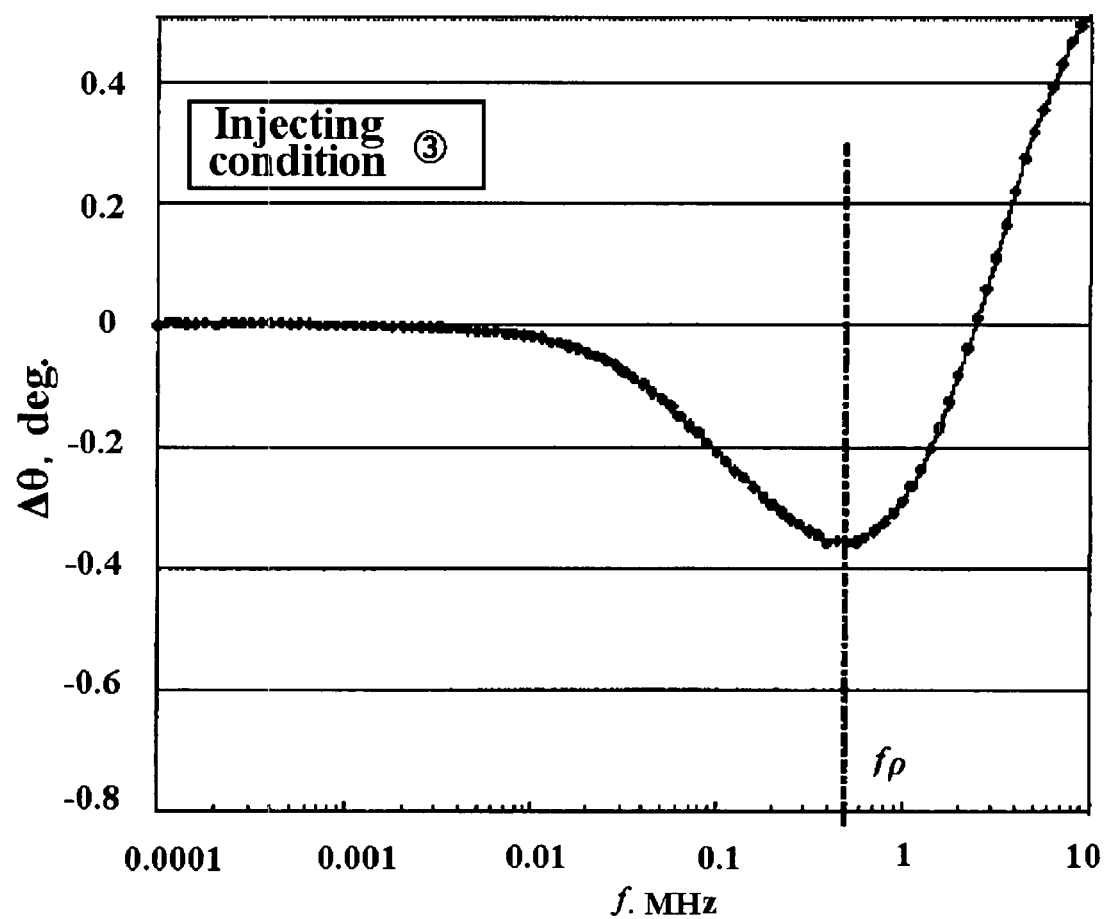
FIG. 16 is an f-$\Delta\theta$ diagram of SKD61 steel processed by shot peening in Injecting condition 3.
Figure 17:
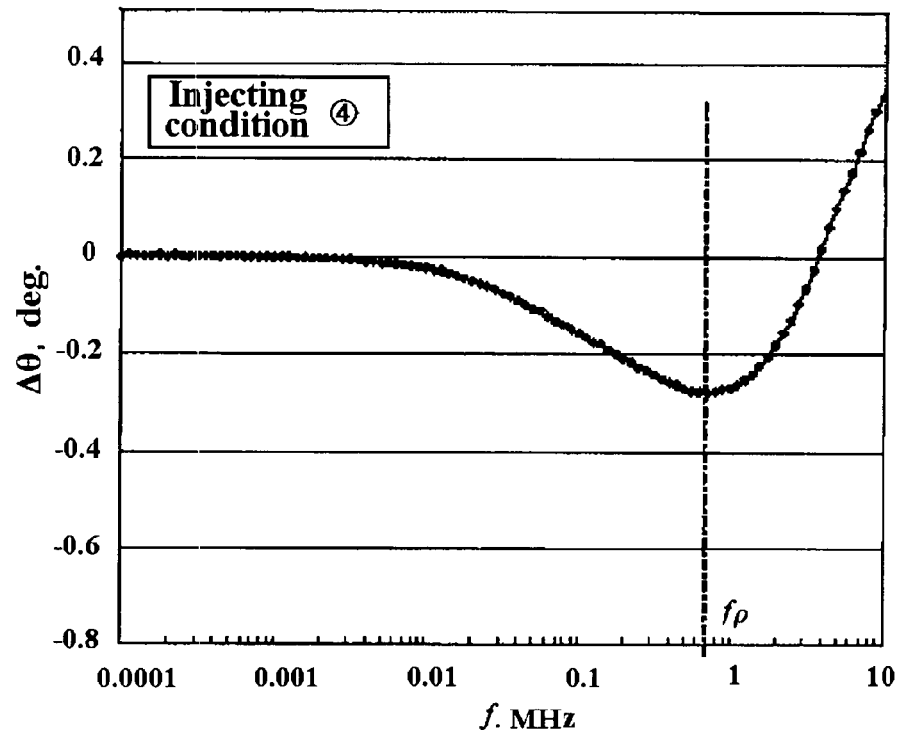
FIG. 17 is an f-$\Delta\theta$ diagram of SKD61 steel processed by shot peening in Injecting condition 4.

FIG. 13 shows results of the relation between the depth from the surface and a distribution of residual stress for each of the prepared samples inspected by X-rays.

When the states of generation of residual stress are compared under different injecting conditions, the injection speed becomes highest and large residual stress reaches the deepest part in Injecting condition 1.

The next highest injection speed is achieved in Injecting condition 2, and the next higher speed is achieved in Injecting condition 3. On the other hand, the lowest injection speed is found in Injecting condition 4. FIG. 13 shows that, as the injection speed is decreased, the residual stress is decreased and the depth of residual stress becomes shallow.

FIGS. 14 to 17 show f-$\Delta\theta$ diagrams obtained by applying the method of the present invention to the samples of Injecting conditions 1 to 4 before residual stress is measured by X-rays.

The shape of each f-$\Delta\theta$ diagram apparently depends on the injecting condition. As shown in the results, the deeper the depth of the residual stress generation layer, the lower frequency $f_P$ giving extreme value $\Delta\theta_P$ of $\Delta\theta$. Since the absolute local minimum value $|\Delta\theta_P|$ varies in response to the magnitude and depth of residual stress, the relation of correspondence obtained by the above calculation is also proven in the actual measurement.

Accordingly, if an f-$\Delta\theta$ diagram of a sample to be subjected to a nondestructive inspection is measured and then compared to the results in FIGS. 14 to 17, the states of generation of residual stress can be determined.

At this time, frequency $f_P$ giving the extreme value or the absolute local minimum value $|\Delta\theta_P|$ is useful.

Figure 18:
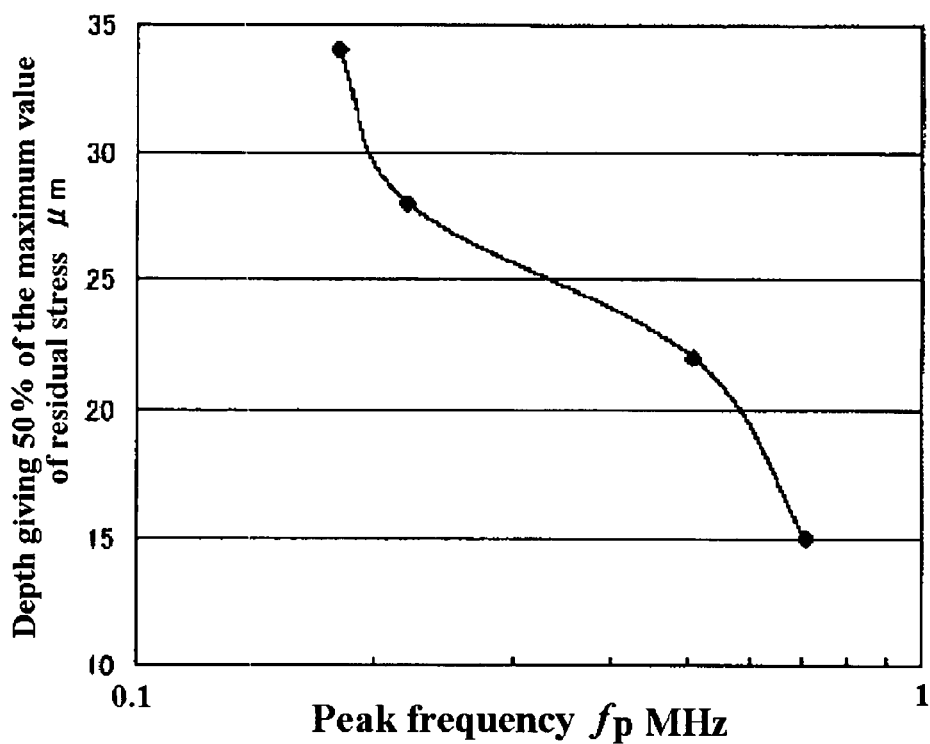
FIG. 18 is a graph showing the relation between the depth at which residual stress becomes 50% which is the maximum value and peak frequency $f_P$ for SKD61 steel processed by shot peening in Injecting conditions 1 to 4.

For example, if a depth at which residual stress becomes half of the maximum value is taken as a typical value of the depth of the residual stress generation layer in which residual stress generates and the relation between the depth and $f_P$ is found from FIGS. 13 to 17, FIG. 18 can be acquired. FIG. 18 is a calibration curve useful for the nondestructive inspection of depths at which residual stress generates.

Example of an Actual Measurement Using SCr420 Steel as a Sample

As Embodiment 2, the following shows results of actual measurement of the state of generation of residual stress and the relation of correspondence between $\Delta\theta$ and $f_P$ when carburized and quenched SCr420 steel processed by shot peening with fine particles is used as a sample.

Figure 19:
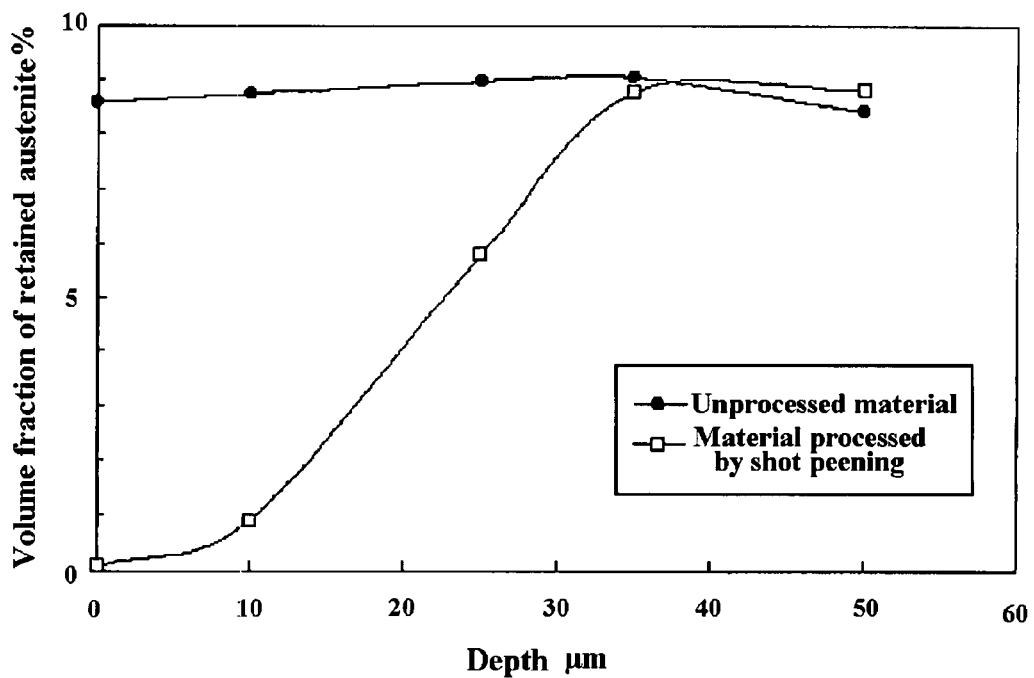
FIG. 19 is a graph showing the relation between the depth from a surface and the volume fraction of retained austenite for SCr420 steel processed by shot peening and SCr420 steel not processed by shot peening.

FIG. 19 shows results of measurement of a distribution in depth of retained austenite before and after the SCr420 steel is processed by shot peening with fine particles. The carburized and quenched. SCr420 steel includes retained austenite, after being processed by shot peening with fine particles, the retained austenite transforms into martensite, thereby, a content of the retained austenite is decreased.

Figure 20:
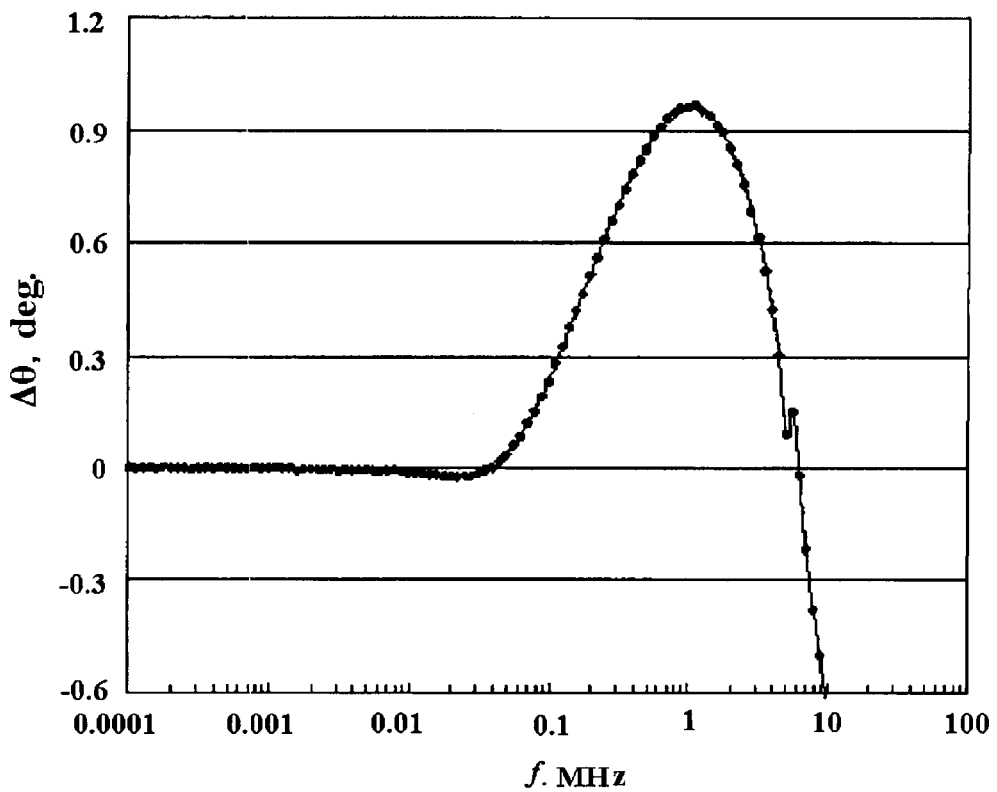
FIG. 20 is a graph showing f-$\theta$ characteristics of SCr420 steel processed by shot peening.

FIG. 20 is an f-$\Delta\theta$ diagram obtained by applying the method of the present invention before X-ray measurements. Since the magnetic permeability is increased when retained austenite transforms into martensite, it can be recognized that the f-$\Delta\theta$ diagram has the local maximum value, thereby, the presence of the same relation as that obtained from the above calculation result is proved.

Since the magnetic permeability is increased when the retained austenite transforms into martensite as described above and such changes in the magnetic permeability appear as changes in the f-Δθ diagram, it is possible to perform the nondestructive inspection of changes in the content of the retained austenite on the sample surface by using the f-Δθ diagram.

Nondestructive Inspection Method

As described with reference to FIGS. 6 to 20, it has been confirmed that an f-Δθ diagram that shows, for example, the frequency response characteristics of impedance of the inspection circuit apparently shows a characteristic feature of the electromagnetic characteristics of a surface of the material to be treated due to effects of residual stress generated by shot peening and characteristic changes are shown in response to the state of generation of residual stress.

In particular, extreme value $\Delta\theta_P$ of $\Delta\theta$ and frequency $f_P$ giving extreme value $\Delta\theta_P$ change characteristically depending on the depth of the residual stress generation layer and the electrical characteristics such as the magnetic permeability and resistivity (conductivity) of the residual stress generation layer.

The nondestructive inspection method according to the present invention focuses this relation of correspondence, so that the frequency response characteristics of impedance of a coil (inspection circuit including the coil) arranged on a sample of which a distribution of residual stress is found is obtained, for example, as an f-Δθ diagram, and the frequency response characteristics of impedance of a similar coil (inspection circuit including the coil) arranged on a sample to be inspected is obtained as a similar method (for example, an f-Δθ diagram), then the frequency response characteristics of impedances in the both circuits are compared by using the f-Δθ diagrams in order to inspect the state of generation of residual stress in the inspection target without destroying the inspection target.

This type of inspection according to the present invention may also inspect, for example, whether there is a match within an allowable range of error between the f-Δθ diagram of a sample and that of an inspection target, or not; for example, a product processed by shot peening that underwent a shot peening process line can be used as an inspection target to determine whether the residual stress in the inspected product falls within the allowable range of error (whether processing failure occurs) as compared to a sample, or not.

Alternatively, samples with different states of generation of residual stress are prepared in advance and the relation of correspondence between changes in f-Δθ diagrams and changes in states of generation of residual stress such as changes in the depth at which residual stress is generated, the magnetic permeability and the resistivity (or conductivity) of the residual stress generation layer is obtained, so that, for an inspection target of which the state of generation of residual stress is unknown, the depth of the residual stress generation layer, the magnetic permeability and the resistivity (or conductivity) of the residual stress generation layer may be inspected or measured.

If the residual stress values (for example, residual stress values on the surface) of the samples are measured and the relation of correspondence between the measured values and the above f-Δθ diagrams is obtained in advance, a residual stress value can be found. Furthermore, when the inspection-target is austenite steel, the relation of correspondence between changes in the amount of austenite and changes in the f-Δθ diagram may be recorded in advance to inspect or measure the amount of retained austenite.

In comparison of the f-Δθ diagrams of the samples and the f-Δθ diagram of the inspection target, an extreme value $\Delta\theta_P$ of $\Delta\theta$, an absolute value $|\Delta\theta_P|$ of $\Delta\theta_P$, and a frequency $f_P$ giving the extreme value show prominent change depending on a change of the state of generation of residual stress as described above, therefore, the method of the present invention can use one or more of $\Delta\theta$, $|\Delta\theta_P|$, and $f_P$ as comparison points when comparing the sample data to the inspection target data.

Nondestructive Inspection Apparatus

Figure 3:
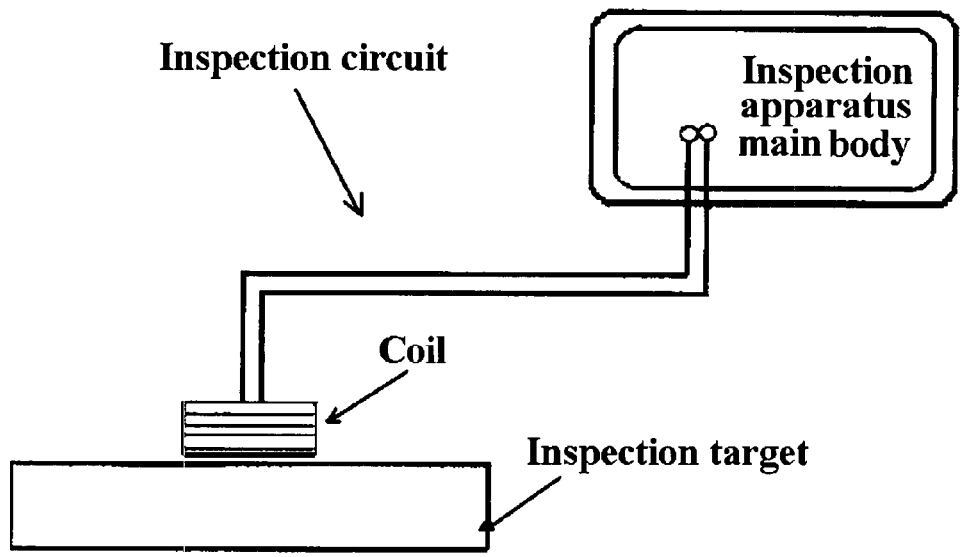
FIG. 3 is a schematic diagram of a nondestructive inspection apparatus according to the present invention.

FIG. 3 illustrates a nondestructive inspection apparatus according to the present invention in order to perform the nondestructive inspection method described above.

As shown in FIG. 3, the nondestructive inspection apparatus according to the present invention comprises an inspection circuit and an inspection apparatus main body connected to the inspection circuit.

The inspection circuit has coils to be arranged on a material to be treated which is processed by shot peening, i.e., the inspection target, and the frequency response characteristics of the impedance of the coils, in more detail, impedance of the inspection circuit including the coils is measured in a state that the coils are arranged at certain intervals to the surface to be treated so that a magnetic field generating direction is orthogonal to the surface to be inspected processed by shot peening in order to inspect the residual stress generated in the inspection target.

In the embodiment shown in the figure, the inspection circuit comprises only the coils and cables connecting the coils and the inspection apparatus main body, but the inspection circuit may include other components as long as it is not deviated from the object of the present invention.

Figure 4:
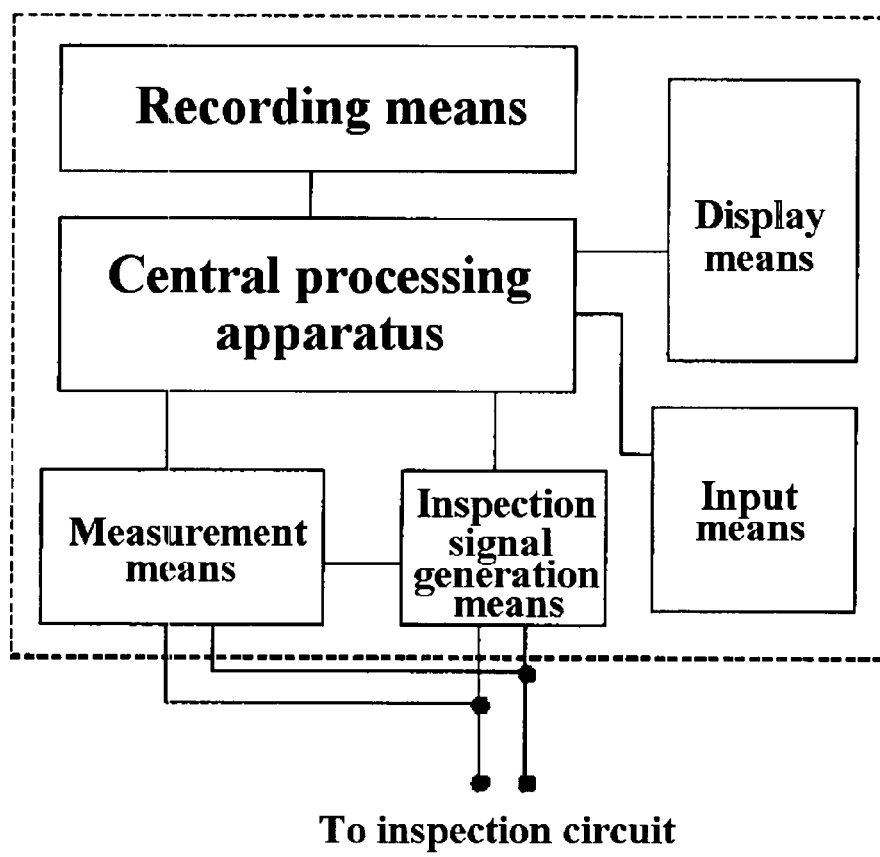
FIG. 4 is a functional block diagram of a main body of the inspection apparatus.

As shown in FIG. 4, the inspection apparatus main body connected to the inspection circuit comprises: an inspection signal generation means for outputting an alternating current inspection signal to the inspection circuit, the inspection signal generation means having an oscillating circuit or the like; a recording means for recording the sample data; a measurement means for measuring the frequency response characteristics of impedance of the inspection circuit, a display means for indicating inspection results visually and/or audibly such as a CRT, a liquid crystal display, and a speaker, and a central processing apparatus for totally controlling operation of the above means.

In addition, an input means such as a keyboard or a touch panel for entering instructions in the central processing apparatus is provided in the inspection apparatus main body.

The central processing apparatus controls the operation of the above means according to the operation specified by a prescribed program or the like, then various control operations required to control the operation of the above means are performed according to execution of the program in the central processing apparatus.

Figure 5:
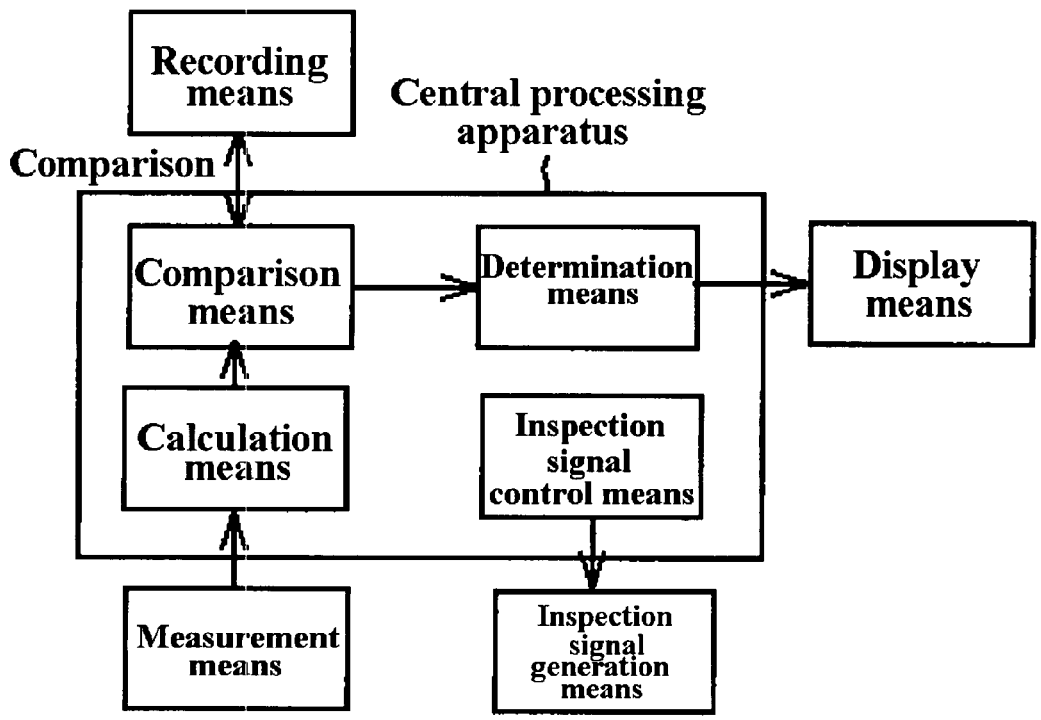
FIG. 5 is a functional block diagram showing means implemented by a central processing apparatus.

FIG. 5 shows a functional block diagram indicating the means implemented by the central processing apparatus.

In FIG. 5, an inspection signal control means changes an input signal for the inspection signal generating means such as an oscillating circuit in order to control the frequency of the inspection signal outputted to the inspection circuit by the inspection signal generating means.

A calculation means calculates, based on the impedance, for example, in the inspection circuit measured by the measurement means, $\Delta\theta$ mentioned above, for example, obtains an extreme value $\Delta\theta_P$ of the calculated $\Delta\theta$ and, if necessary, obtains the absolute value $|\Delta\theta_P|$ of $\Delta\theta_P$, then identifies a frequency $f_P$ of the inspection signal giving extreme value $\Delta\theta_P$.

A comparing means compares calculation results by the calculation means, such as $\Delta\theta_P$, $|\Delta\theta_P|$, and $f_P$ of the inspection target to the sample data previously recorded in the recording means.

Based on the comparison results by the comparing means, a determination means determines a match or non-match between the sample data and the inspection target data and, if the relation of correspondence between changes in $\Delta\theta_P$, $|\Delta\theta_P|$, and $f_P$ and the depth of the residual stress generation layer, the magnetic permeability and resistivity (conductivity) of the residual stress generation layer is recorded in the recording means as the sample data, determines the depth, magnetic permeability, and resistivity (conductivity) of the residual stress generation layer according to the relation of correspondence.

The determination results by the determination means are output to the display means and indicated visually or audibly. For example, when the determination means determines whether the difference between sample data and inspection target data falls within the allowable range of error, for example, determines a processing failure or the like in the inspection target, the result may be indicated as a beep tone with a speaker or indicated as a blink of a warning light and, if the depth, magnetic permeability, and resistivity (conductivity) of the residual stress generation layer are also determined, the result may be indicated as numerical values or the like on a CRT or a liquid crystal display or the like.

Thus, the broadest claims that follow are not directed to a machine that is configuration a specific way. Instead, said broadest claims are intended to protect the heart or essence of this breakthrough invention. This invention is clearly new and useful. Moreover, it was not obvious to those of ordinary skill in the art at the time it was made, in view of the prior art when considered as a whole.

Moreover, in view of the revolutionary nature of this invention, it is clearly a pioneering invention. As such, the claims that follow are entitled to very broad interpretation as to protect the heart of this invention, as a matter of law.

It will thus be seen that the objects set forth above, and those made apparent from the foregoing description, are efficiently attained. Also, since certain changes may be made in the above construction without departing from the scope of the invention, it is intended that whole matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described;

What is claimed is:

1. A nondestructive inspection method for a surface processed by shot peening in which a steel material processed by shot peening is used as an inspection target to inspect residual stress, comprising the steps of:

arranging a coil provided in an inspection circuit on a surface processed by shot peening of a sample of which a state of generation of residual stress is found, the sample being made of the same material as the inspection target, inputting an alternating current signal to the inspection circuit with changing frequency, measuring frequency response characteristics of impedance of the inspection circuit, and acquiring the frequency response characteristics as sample data;

arranging the coil provided in the inspection circuit on a surface of the inspection target, inputting an alternating current signal to the inspection circuit with changing frequency, measuring frequency response characteristics of impedance of the inspection circuit, and acquiring the frequency response characteristics as inspection target data; and comparing the inspection target data to the sample data and, based on the state of generation of residual stress found in the sample, inspecting a state of generation of residual stress in the inspection target.

2. The nondestructive inspection method for the surface processed by shot peening according to claim 1, wherein changes in a phase angle between voltage and current generated in the inspection circuit depending on changes in the frequency of the alternating current signal input to the inspection circuit are measured as the frequency response characteristics of the impedance.

3. The nondestructive inspection method for the surface processed by shot peening according to claim 2, wherein:

the coil provided in the inspection circuit is arranged on a surface of a reference material not processed by shot peening, the reference material being made of the same material as the inspection target, and an alternating signal is input to the inspection circuit with changing frequency to acquire changes in a phase angle between a voltage and a current in the inspection circuit as reference data; and a difference between the reference data and the sample data and a difference between the reference data and the inspection target data are used to compare the sample data to the inspection target data.

4. The nondestructive inspection method for the surface processed by shot peening according to claim 3, wherein a value indicating a peak of the difference of the phase angle with respect to changes in the frequency is obtained as an extreme value so as to use the extreme value and/or a frequency giving the extreme value as comparison points for the inspection target data and the sample data.

5. The nondestructive inspection method for the surface processed by shot peening according to claim 1, wherein a depth of a residual stress generation layer formed on the surface of the inspection target by shot peening is inspected or measured based on comparison between the inspection target data and the sample data.

6. The nondestructive inspection method for a surface processed by shot peening according to claim 1, wherein a magnetic permeability and/or a resistivity of the residual stress generation layer formed by applying residual stress given by shot peening is inspected or measured based on comparison between the inspection target data and the sample data.

7. A nondestructive inspection apparatus for a surface processed by shot peening in which a steel material processed by shot peening is used as an inspection target to inspect residual stress, the apparatus comprising:

an inspection circuit having a coil arranged on the inspection target;

an inspection signal generation means for outputting an alternating current signal to the inspection circuit while changing frequency;

a measurement means for measuring frequency response characteristics of impedance of the inspection circuit;

a recording means for recording frequency response characteristics of impedance measured by arranging the coil of the inspection circuit on a sample of which a state of generation of residual stress is found, as sample data, the sample being made of the same material as the inspection target;

a comparison means for comparing inspection target data with the sample data recorded in the recording means, the inspection target data being the frequency response characteristics of impedance of the inspection circuit measured by arranging the coil of the inspection circuit on the inspection target; and a determination means for determining, based on comparison results by the comparing means, a state of generation of residual stress in the inspection target based on said state of generation of residual stress found in the sample.

8. The nondestructive inspection apparatus for the surface processed by shot peening according to claim 7, wherein:

the measurement means measures, as the inspection target data, changes in a phase angle between a voltage and a current generated in the inspection circuit depending on changes in the frequency of the alternating current signal input to the inspection circuit and;

the recording means records, as the sample data, changes in a phase angle between voltage and current generated in the inspection circuit in the sample depending on changes in the frequency of the input signal.

9. The nondestructive inspection apparatus for the surface processed by shot peening according to claim 8, wherein:

the recording means records, as reference data, changes in a phase angle between a voltage and a current generated in the inspection circuit in a reference material not processed by shot peening, the reference material being made of the same material as the inspection target; and the comparing means compares a difference between the reference data and the sample data to a difference between the reference data and the inspection target data.

10. The nondestructive inspection apparatus for the surface processed by shot peening according to claim 9, wherein a value indicating a peak of the difference of the phase angle with respect to changes in the frequency is obtained as an extreme value so as to use the extreme value and/or a frequency giving the extreme value as comparison points for the inspection target data and the sample data.

11. The nondestructive inspection apparatus for the surface processed by shot peening according to claim 7, wherein:

the recording means records, as the sample data, a relation of correspondence between changes in a depth of the residual stress generation layer and frequency response characteristics of impedance of the inspection circuit changed depending on the changes in the depth of the residual stress generation layer; and the determination means determines, according to comparison results by the comparing means, the depth of the residual stress generation layer formed on a surface of an inspection target based on the relation of correspondence.

12. The nondestructive inspection apparatus for the surface processed by shot peening according to claim 7, wherein:

the recording means records, as the sample data, relation of correspondence between changes in a magnetic permeability and/or a resistivity of the residual stress generation layer and frequency response characteristics of impedance of the inspection circuit changed depending on the changes in the magnetic permeability and/or the resistivity; and the determination means determines, according to comparison results by the comparing means, determine the magnetic permeability and/or the resistivity of the residual stress generation layer formed on the surface of the inspection target based on the relation of correspondence.

* * * * *